US011786535B1

(12) United States Patent
Kandeel et al.

(10) Patent No.: US 11,786,535 B1
(45) Date of Patent: Oct. 17, 2023

(54) METHODS OF INHIBITING CYCLOOXYGENASE

(71) Applicant: KING FAISAL UNIVERSITY, Hofouf (SA)

(72) Inventors: Mahmoud Kandeel, Hofouf (SA); Shady Burayk, Hofouf (SA)

(73) Assignee: KING FAISAL UNIVERSITY, Hofouf (SA)

( * ) Notice: Subject to any disclaimer, the term of this patent is extended or adjusted under 35 U.S.C. 154(b) by 0 days.

(21) Appl. No.: 18/112,854

(22) Filed: Feb. 22, 2023

(51) Int. Cl.
*A61K 31/5377* (2006.01)
*A61K 31/4745* (2006.01)
*A61K 31/4155* (2006.01)
*A61K 31/341* (2006.01)

(52) U.S. Cl.
CPC ........ *A61K 31/5377* (2013.01); *A61K 31/341* (2013.01); *A61K 31/4155* (2013.01); *A61K 31/4745* (2013.01)

(58) Field of Classification Search
CPC .............. A61K 31/5377; A61K 31/341; A61K 31/4155; A61K 31/4745
See application file for complete search history.

(56) References Cited

U.S. PATENT DOCUMENTS

| 5,141,950 A | 8/1992 | Nakane et al. |
| 6,566,359 B1 | 5/2003 | Bazan et al. |
| 7,309,716 B2 | 12/2007 | Wilson et al. |
| 8,138,168 B1 | 3/2012 | Jones et al. |
| 11,478,464 B1 | 10/2022 | Elsayed et al. |

OTHER PUBLICATIONS

Burayk, S. et al., "Drug Discovery of New Anti-Inflammatory Compounds by Targeting Cyclooxygenases," Pharmaceuticals 15: 282 (Feb. 24, 2022).
Veerasamy, R., "Structure-Activity Relationship Analysis of Benzimidazoles as Emerging Anti-Inflammatory Agents: An Overview," Pharmaceuticals 14(7): 663 (2021).
Pubchem Compound 16677172 (2007).
Pubchem Compound 56886083 (2012).
Pubchem Compound 136060329 (2019).
Pubchem Compound 28735022 (2009).

*Primary Examiner* — Kortney L. Klinkel
*Assistant Examiner* — Padmaja S Rao
(74) *Attorney, Agent, or Firm* — Nath, Goldberg & Meyer; Richard C. Litman

(57) ABSTRACT

A method of inhibiting cyclooxygenase includes administering an inhibitory agent to a patient in need thereof. The inhibitory agent is selected from Compound 1 (5-{[(4-fluorobenzyl)(tetrahydrofuran-2-ylmethyl)amino]methyl}-2-methoxyphenyl)methanol), Compound 2 (N-{[3-(3-methoxyphenyl)-1-phenyl-1H-pyrazol-4-yl]methyl}-N-methyl-2-(1H-pyrazol-4-yl)ethanamine), Compound 3 ({4-[3-(2-pyridinyl)benzyl]-3-morpholinyl}acetic acid), and Compound 4 ([4-chloro-2-(7-oxo-5,6,7,8-tetrahydro-1H-pyrazole[4,3-g]quinoline-5-yl)phenoxy]acetic acid). Compounds 1-4 may inhibit both the COX-1 and the COX-2 enzymes.

7 Claims, No Drawings

METHODS OF INHIBITING CYCLOOXYGENASE

BACKGROUND

1. Field

The disclosure of the present patent application relates to methods of inhibiting cyclooxygenase using non-steroidal anti-inflammatory compounds (also known as Non-Steroidal Anti-Inflammatory Drugs—NSAIDs, or Non-Steroidal Anti-Inflammatory Agents—NSAIAs).

2. Description of the Related Art

In the treatment of inflammatory episodes, nonsteroidal anti-inflammatory medications (NSAIDs) constitute the gold standard. NSAIDs, by definition, reduce inflammation and relieve pain, but are not related to steroids (which also reduce inflammation). NSAIDs block production of certain body chemicals associated with inflammation, thereby treating pain, fever, and other inflammatory effects on the body. One of the most common NSAIDs is aspirin.

Inflammation is associated with redness, pain, and swelling Inflammation may be acute, or it may be chronic. Some diseases are associated with chronic inflammation—such as arthritis and rheumatoid arthritis, diabetes, asthma, autoimmune diseases, Alzheimer's, and cardiovascular disease, among many others. Prostaglandins act as mediators of acute inflammation and may also play a part in chronic inflammation.

Certain NSAIDs reduce production of prostaglandins, which play a key role in generating the inflammatory response. Specifically, such NSAIDs block cyclooxygenase (COX) enzymes, which are involved in formation of prostaglandins. Inhibition of COX enzymes impairs or inhibits prostaglandin synthesis, resulting in reduction of inflammation and in associated effects of inflammation.

In this context, cyclooxygenases 1 and 2 (COX-1 and COX-2) and arachidonate 5-lipooxygenase (5-lox) play key roles in the production and regulation of inflammation. COX-1 is expressed predominantly in the gastrointestinal tract, while COX-2 is predominantly produced at sites of inflammation. The stomach lining and renal functions are protected by certain prostaglandins produced by COX-1. COX-2 is activated in response to inflammation and is, therefore, inducible in nature. The enzyme 5-lox is involved in transforming essential fatty acid substrates into leukotrienes (as well as other biologically active products). Leukotrienes (LTs) are the first class of mediators that contribute to the inflammatory process. LTs play a significant part in the inflammatory process overall.

Prostaglandin E2 (PGE2) and prostaglandin I2 (PGI2, or prostacyclin) increase blood flow in inflamed areas by their potent vasodilators action. PGI2 is responsible for platelet aggregation and vascular endothelium inhibition. The vasodilation effect of Prostaglandin E2 and Prostacyclin I2 acts to protect the gastric mucosa by increasing the secretion of mucus and preventing increase of acidity and pepsin content in the stomach. In the kidneys, PGE and PGI play a role in increasing the blood flow and regulation of the glomerular filtration rate.

Non-steroidal anti-inflammatory drugs are the gold standard in treating inflammatory episodes due to their ability to block the arachidonic acid pathways. Certain NSAIDs act by selective or non-selective inhibition of COX-1 and COX-2 enzymes. In addition to lowering inflammation, however, currently available non-selective medicines inhibit platelet aggregation. Additionally, the existing non-selective medications raise the risk of stomach ulcers and bleeding.

Accordingly, development of new NSAIDs that result in reduced frequency and severity of negative side effects is desired.

3. SUMMARY

A method of inhibiting cyclooxygenase can include administering a therapeutically effective amount of an inhibitory compound to a patient in need thereof, the inhibitory compound being selected from the group consisting of

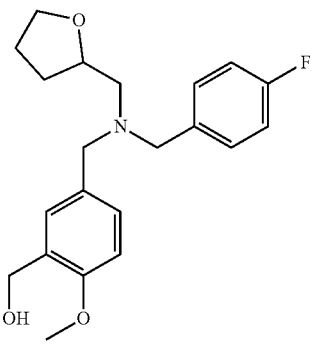 [SMILES: COc1ccc(CN(Cc2ccc(F)cc2)CC2CCCO2)cc1CO]

Compound 1 (5-{[(4-fluorobenzyl)(tetrahydrofuran-2-ylmethyl)amino]methyl}-2-methoxyphenyl)methanol)

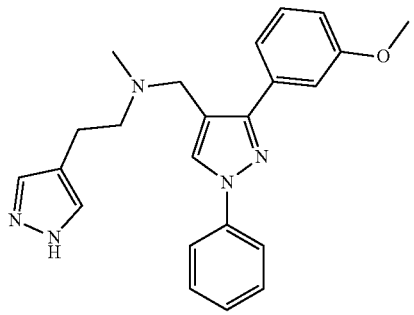 [SMILES: COc1cccc(-c2nn(-c3ccccc3)cc2CN(C)CCc2cn[nH]c2)c1]

Compound 2 (N-{[3-(3-methoxyphenyl)-1-phenyl-1H-pyrazol-4-yl]methyl}-N-methyl-2-(1H-pyrazol-4-yl)ethanamine)

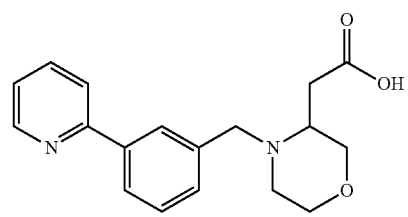 [SMILES: O=C(O)CC1COCCN1Cc1cccc(-c2ccccn2)c1]

Compound 3 ({4-[3-(2-pyridinyl)benzyl]-3-morpholinyl}acetic acid); and

Compound 2 (N-{[3-(3-methoxyphenyl)-1-phenyl-1H-pyrazol-4-yl]methyl}-N-methyl-2-(1H-pyrazol-4-yl)ethanamine)

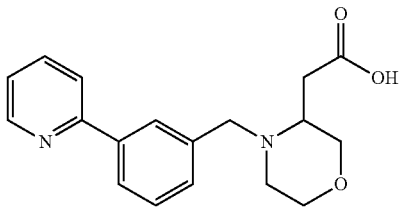

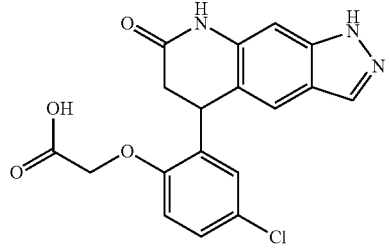 [SMILES: O=C(O)COc1ccc(Cl)cc1C1CC(=O)Nc2cc3[nH]ncc3cc21]

Compound 3 ({4-[3-(2-pyridinyl)benzyl]-3-morpholinyl}acetic acid); and

Compound 4 ([4-chloro-2-(7-oxo-5,6,7,8-tetra-hydro-1H-pyrazole[4,3-g]quinoline-5-yl)phenoxy]acetic acid)

These and other features of the methods of inhibiting cyclooxygenase will become readily apparent upon further review of the following specification and drawings.

4. DETAILED DESCRIPTION OF THE EMBODIMENTS

A method of inhibiting cyclooxygenase can include administering a therapeutically effective amount of an inhibitory compound to a patient in need thereof, the inhibitory compound being selected from the group consisting of

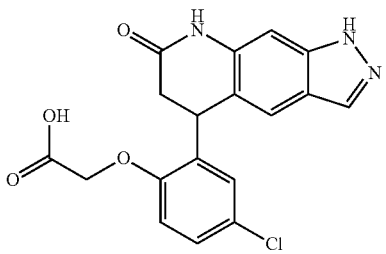

Compound 4 ([4-chloro-2-(7-oxo-5,6,7,8-tetra-hydro-1H-pyrazole[4,3-g]quinoline-5-yl)phenoxy]acetic acid)

In an embodiment, the method can include administering a pharmaceutical composition including the inhibitory compound and a pharmaceutically acceptable carrier. The phrase "pharmaceutically acceptable," as used herein, refers to molecular entities and compositions that do not produce an allergic or similar untoward reaction when administered to a human. As used herein, a "carrier" includes any and all solvents, dispersion media, vehicles, coatings, diluents, isotonic and absorption delaying agents, buffers, carrier solutions, suspensions, colloids, excipients, and the like. A therapeutically effective amount of the compound or an amount effective to treat inflammation may be determined initially from the Examples described herein and adjusted for specific targeted diseases using routine methods. The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose.

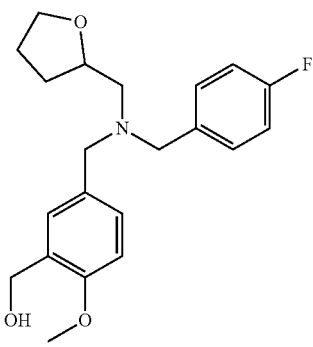 [SMILES: COc1ccc(CN(Cc2ccc(F)cc2)CC2CCCO2)cc1CO]

Compound 1 (5-{[(4-fluorobenzyl)(tetrahydrofuran-2-ylmethyl)amino]methyl}-2-methoxyphenyl)methanol)

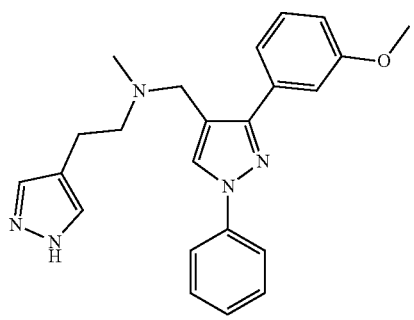 [SMILES: COc1cccc(-c2nn(-c3ccccc3)cc2CN(C)CCc2cn[nH]c2)c1]

As described in detail below, an initial virtual screening of over one million compounds was conducted to identify candidate compounds with structures suitable for targeting the structure of proteins highly associated with inflammation. Further assessment of the candidates identified by the virtual screening was then conducted based on computational pharmacokinetic features, drug-likeness, percent of oral absorption in humans, anticipated carcinogenicity, mutagenicity, and toxicity testing. Ultimately, seven compounds were chosen for further in vitro assessment for their inhibitory effects against COX-1 and COX-2 as well as cytotoxicity studies against Human embryonic kidney (HEK293) cells based on their powerful docking score, overall safety profiles, and favorable drug-likeness features.

During the virtual screening, 1.65 million compounds were considered against the structures of three proteins highly associated with inflammation and its pathogenesis: COX-1, COX-2, and 5-lox. The thirty candidates with the greatest scores were then assessed for computational pharmacokinetic features, drug-likeness, percent of oral absorption in humans, anticipated carcinogenicity, mutagenicity, and toxicity testing. All compounds demonstrated drug-like characteristics and excellent pharmacokinetic features. However, only seven compounds were devoid of anticipated carcinogenicity in mice and rats, with a high oral absorption rate and no violations of Lipinski's rule of five. Lipinski's rule of five is used as a convenient aid in determining orally bioavailable drugs, helping to determine a candidate compound's drug-likeness and whether it is likely to be an orally active drug in humans. The seven compounds showing high binding scores in vitro for all three proteins were then further assessed for their relative inhibitory effects specifically against COX-1 and COX-2, as well as cytotoxicity studies against human embryonic kidney (HEK293) cells based on their powerful docking score, overall safety profiles, and favorable drug-likeness features. The compounds demonstrated safety profiles and no cytotoxicity.

After 25 hours of treatment, none of these seven chemicals at a concentration of 40 µM induced obvious morphological abnormalities or damages in HEK293 cells in a cytotoxicity assay. Thus, the candidates were demonstrated to be safer than celecoxib at a comparable molar concentration, at least by this measure. These seven compounds were then examined for their inhibitory action on COX-1 and COX-2 as compared to reference NSAIDs indomethacin, diclofenac, celecoxib, and rofecoxib. All of the compounds were demonstrated to be potent inhibitors of the COX enzymes. Compounds 1-4 were identified as non-selective cyclooxygenase inhibitors.

Compound 1 (5-{[(4-fluorobenzyl)(tetrahydrofuran-2-yl-methyl)amino]methyl}-2-methoxyphenyl)methanol), Compound 2 (N-{[3-(3-methoxyphenyl)-1-phenyl-1H-pyrazol-4-yl]methyl}-N-methyl-2-(1H-pyrazol-4-yl)ethanamine), Compound 3 ({4-[3-(2-pyridinyl)benzyl]-3-morpholinyl}acetic acid), and Compound 4 ([4-chloro-2-(7-oxo-5,6,7,8-tetrahydro-1H-pyrazole[4,3-g]quinoline-5-yl)phenoxy]acetic acid) each proved to be excellent candidates for use as non-selective NSAIDs for inhibiting cyclooxygenase 1 and/or 2.

The results identify Compounds 1-4 as four compounds with favorable drug-likeness, powerful inhibition of cyclooxygenase 1 and 2, and safe profiles on cells. As a result, these molecules have exciting potential as new anti-inflammatory medicines—new NSAIDs or NSAIAs. Table 1 identifies the formal chemical name and source for each of Compounds 1-4.

TABLE 1

Chemical name for Compound 1 and Compound 2

| Compound | Chemical name | Vendor | ID |
| --- | --- | --- | --- |
| Compound 1 | 5-{[(4-fluorobenzyl)(tetrahydrofuran-2-ylmethyl)amino]methyl}-2-methoxyphenyl)methanol | Chembridge Corporation (San Diego, CA, USA) | Compound 1 43255511 |
| Compound 2 | N-{[3-(3-methoxyphenyl)-1-phenyl-1H-pyrazol-4-yl]methyl}-N-methyl-2-(1H-pyrazol-4-yl)ethanamine | Chembridge Corporation (San Diego, CA, USA) | Compound 2 20053063 |
| Compound 3 | {4-[3-(2-pyridinyl)benzyl]-3-morpholinyl}acetic acid | Chembridge Corporation (San Diego, CA, USA) | Compound 3 21586151 |
| Compound 4 | [4-chloro-2-(7-oxo-5,6,7,8-tetrahydro-1H-pyrazole[4,3-g]quinoline-5-yl)phenoxy]acetic acid | Chembridge Corporation (San Diego, CA, USA) | Compound 4 86480078 |

The present teachings are illustrated by the following examples.

EXAMPLES

Example 1

Materials and Methods

The Schrodinger Maestro molecular modeling package (Schrodinger LLC, New York, USA) was used in all virtual screening modeling steps. QikProp software tools are an accurate, rapid, and simple-to-use method for predicting molecular properties. The QikProp software application compares the properties of a specified molecule with the properties of compounds found in 95 percent of commonly prescribed medications. To find any probable places between the active-site space of the receptor and the ligand, a gradable sequence of filters is used to attempt to locate them. A grid composed of different sets of fields that eventually give various correct gradings of the ligand poses while also justifying and representing the structure and features of the receptor is created.

COX-1 and COX-2 inhibitor screening assay kits were obtained from Cayman Chemical (Ann Arbor, Mich., USA).

Example 2

Identifying COX-2 Inhibitor Structure

The protein data bank website was browsed in order to retrieve the COX-2 structural PDB ID SIKQ. Through use of the protein preparation module in the Schrodinger Maestro molecular modeling tool, the structure was optimized for virtual screening and docking purposes. Crystallographic chemicals and water molecules were removed from the solution. The protein was protonated by the addition of polar hydrogens, and the structures were optimized and energy minimized by use of the OPLS2005 force field.

The Maestro grid-generating module was used to build the docking grids, which used the defined ligand-binding cavities in the analyzed structures as a starting point. A 20-nanometer grid was incorporated around the enzyme's active site.

Standard precision docking (SP) followed by extra precision docking (XP) was used in a two-step docking run to obtain the top candidates. For Van der Waals radius scaling, an integer value of 0.8 was used. Extra precision docking is designed to lower the likelihood of a false-positive result. High docking-score compounds (<−12) were chosen for interaction study with pocket residues, and their binding properties and pocket filling pattern were studied visually. The results for Compounds 1-4 are presented in Table 2 below.

Example 3

Enzyme (COXs) Inhibition Assay

The inhibitory effects of candidate compounds on COX-1 and COX-2 were determined using COX inhibitor screening test kits, testing each compound's capacity to inhibit the

TABLE 2

Docking Score of Compounds 1-4 With Cox-2 (PDB: 5IKQ)

| compound | Name | Docking Score (kcal/mol) | Glide Hbond | Glide Lipo | Glide Ligand Efficiency |
|---|---|---|---|---|---|
| 1 | 5-{[(4-fluorobenzyl)(tetrahydrofuran-2-ylmethyl)amino]methyl}-2-methoxyphenyl)methanol | −12.41 | 0 | −5.106 | −0.477 |
| 2 | N-{[3-(3-methoxyphenyl)-1-phenyl-1H-pyrazol-4-yl]methyl}-N-methyl-2-(1H-pyrazol-4-yl)ethanamine | −13.14 | −0.87 | −5.373 | −0.453 |
| 3 | {4-[3-(2-pyridinyl)benzyl]-3-morpholinyl}acetic acid | −13.408 | 0 | −3.123 | −0.583 |
| 4 | [4-chloro-2-(7-0x0-5,6,7,8-tetrahydro-1H-pyrazole[4,3-g]quinoline-5-yl)phenoxy ]acetic acid | −13.222 | −0.813 | −4.053 | −0.509 |

Example 3

Compound Drug-Likeness and ADME Pharmacokinetic Properties and Descriptors

Descriptors used included the compound's molecular weight, hydrogen bond donor and acceptor, oral absorption percentage and Lipinski's rule of five violations. The preADMET web-based software application was used to predict carcinogenicity.

Drug likeliness and bioavailability properties of the compounds were assessed using Qikprop v4.2. Compound carcinogenicity was determined by preADMET server (preadmet.bmdrc.kr). All compounds passed Lipinski's rule of five without any violation with estimated high absorption rates. As reflected in Table 3, Compounds 1 and 2 were assessed for MW, Donor and Accept HB, Human oral absorption percentage, violations of Lipinski's rule of five, and carcinogenicity in mice and rats. Further, it would be expected that the present compounds exhibit a reduced inhibition of platelet aggregation as compared to other currently available NSAIDs.

TABLE 3

Drug-likeness and ADME Properties of Compounds 1-4

| | Compound 1 | Compound 2 | Compound 3 | Compound 4 |
|---|---|---|---|---|
| MW | 371.779 | 387.483 | 359.44 | 312.368 |
| Donor HB | 3 | 1 | 1 | 1 |
| Accept HB | 6.25 | 5.25 | 6.15 | 6.7 |
| Human oral absorption % | 60.987 | 100 | 100 | 61.58 |
| Violations of the Rule of five | 0 | 0 | 0 | 0 |
| Carcinogenicity in mouse | Negative | Negative | Negative | Negative |
| Carcinogenicity in rat | Negative | Negative | Negative | Negative | conversion of arachidonic acid to prostaglandin. In test tubes, 25 mM Tris-HCl, pH 8.0, containing 5 mM EDTA, phenol, and 1 mM hematin was added. The test compounds were dissolved in DMSO and added in concentrations ranging from 0.005-200 Dimethyl sulfoxide alone was applied to control test containers. COX-1 or COX-2 enzymes were added to the test tubes, which were then preincubated for 10 minutes at 37° C. The arachidonic acid substrate was added, and the tubes were further incubated at 37° C. for 2 minutes. The compound's immunochemical assay was used to calculate the amount of prostaglandin produced.

Three separate experiments were used to calculate the IC50 values. The selectivity index was calculated as follows:

$$\text{Selectivity Index } (SI) = \frac{IC_{50} \text{ COX-1}}{IC_{50} \text{ COX-2}}$$

Results of these experiments are summarized in Table 4.

TABLE 4

Estimated IC50 Values (in μM) For Compounds 1-4 Against COX-1 and COX-2. Celecoxib, rofecoxib, indomethacin and diclofenac were control drugs

| Compound | COX-1 IC$_{50}$ (μM) | COX-2 IC$_{50}$ (μM) | SI |
|---|---|---|---|
| Celecoxib | 14.7 ± 1.045 | 0.045 ± 0.005 | 326.6 |
| Rofecoxib | 14.5 ± 1.125 | 0.025 ± 0.005 | 580 |
| Indomethacin | 0.1 ± 0.015 | 0.0725 ± 0.01 | 1.38 |
| Diclofenac | 0.05 ± 0.006 | 0.02 ± 0.001 | 2.5 |
| Compound 1 | 7.62 ± 0.05 | 0.21 ± 0.01 | 36.3 |
| Compound 2 | 10.57 ± 0.33 | 0.08 ± 0.009 | 132.64 |
| Compound 3 | 11.52 ± 0.13 | 0.06 ± 0.075 | 190.88 |
| Compound 4 | 9.19 ± 0.046 | 0.097 ± 0.015 | 95.068 |

It is to be understood that the method of inhibiting cyclooxygenase described herein is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of inhibiting cyclooxygenase in a patient, comprising administering to a patient in need thereof a therapeutically effective amount of a pharmaceutical composition comprising an inhibitory compound and a pharmaceutically acceptable carrier, the inhibitory compound being selected from the group consisting of:

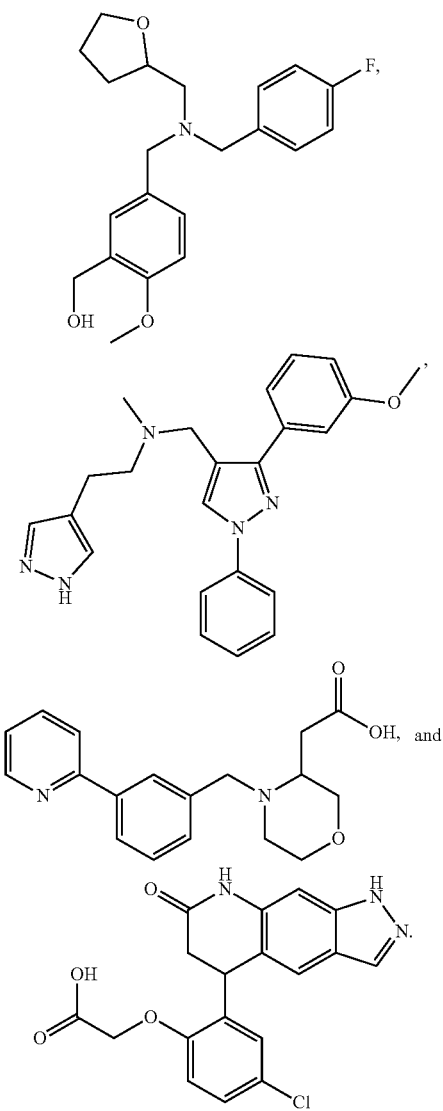

2. The method of claim 1, wherein the inhibitory compound inhibits cyclooxygenase 1 (COX-1) and cyclooxygenase 2 (COX-2).

3. The method of claim 1, wherein the compound is administered orally to the patient.

4. The method of claim 1, wherein the inhibitory compound is:

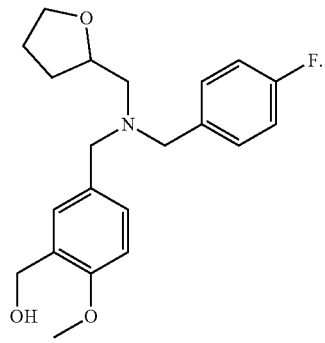 [SMILES: COc1ccc(CN(Cc2ccc(F)cc2)CC2CCCO2)cc1CO]

5. The method of claim 1, wherein the inhibitory compound is:

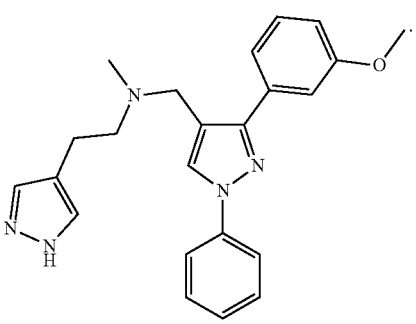 [SMILES: COc1cccc(-c2nn(-c3ccccc3)cc2CN(C)CCc2cn[nH]c2)c1]

6. The method of claim 1, wherein the inhibitory compound is:

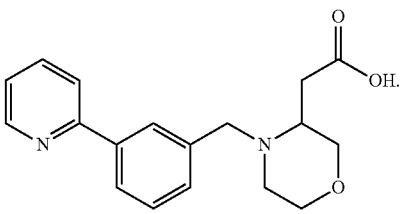 [SMILES: O=C(O)CC1COCCN1Cc1cccc(-c2ccccn2)c1]

7. The method of claim 1, wherein the inhibitory compound is:

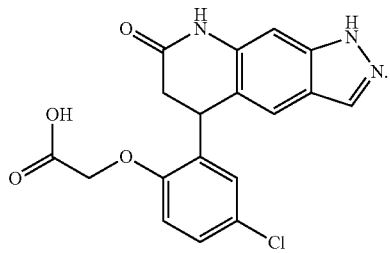 [SMILES: O=C(O)COc1ccc(Cl)cc1C1CC(=O)Nc2cc3[nH]ncc3cc21]

* * * * *